United States Patent
Fruscello

Patent Number: 6,099,486
Date of Patent: Aug. 8, 2000

[54] PRECORDIAL MONITORING APPARATUS

[76] Inventor: John Fruscello, 50 Rocky Creek Rd., C-38, Greenville, S.C. 29615

[21] Appl. No.: 08/915,393

[22] Filed: Aug. 20, 1997

[51] Int. Cl.⁷ .................................................. A61B 7/00
[52] U.S. Cl. .......................... 600/586; 600/528; 600/549; 181/126
[58] Field of Search .................... 181/126, 131, 181/133, 135, 136, 137; 600/528, 549, 372, 382, 386, 391, 484, 586

[56] References Cited

U.S. PATENT DOCUMENTS

| | | | |
|---|---|---|---|
| D. 373,824 | 9/1996 | Packard et al. | D24/134 |
| 4,177,871 | 12/1979 | Clanton | 181/131 |
| 4,328,814 | 5/1982 | Arkans | 128/640 |
| 4,401,125 | 8/1983 | Taylor et al. | 128/715 |
| 4,705,048 | 11/1987 | Pfohl | 600/528 |
| 4,777,961 | 10/1988 | Saltzman | 128/715 |
| 4,926,866 | 5/1990 | Lee | 600/301 |
| 4,991,686 | 2/1991 | Allen | 181/131 |
| 4,995,473 | 2/1991 | Packard | 181/137 |
| 5,010,890 | 4/1991 | Pfohl et al. | 600/586 |
| 5,027,825 | 7/1991 | Phelps, Sr. et al. | 128/715 |
| 5,324,471 | 6/1994 | Packard et al. | 264/279 |
| 5,420,382 | 5/1995 | Katz | 181/131 |
| 5,573,012 | 11/1996 | McEwan | 600/534 |
| 5,611,349 | 3/1997 | Halleck et al. | 128/721 |
| 5,638,453 | 6/1997 | McLaughlin | 381/67 |
| 5,853,005 | 12/1998 | Scanlon | 600/459 |
| 5,913,826 | 6/1999 | Blank | 600/547 |

Primary Examiner—Max Hindenburg
Assistant Examiner—Charles Marmor, III
Attorney, Agent, or Firm—Dority & Manning

[57] ABSTRACT

A precordial monitor including a head that has a chamber for capturing sound from a patient's body. The head has an acoustic probe for detecting the sound captured in the chamber and a temperature sensor for measuring the skin temperature of the patient.

7 Claims, 2 Drawing Sheets

PRECORDIAL MONITORING APPARATUS

BACKGROUND OF THE INVENTION

1. Field of the Invention

The invention relates generally to the field of stethoscopes, and more particularly to stethoscopes that can be secured to a patient's body for extended periods of time.

2. Description of Related Art

The stethoscope is perhaps the most widely recognized medical instrument. Nevertheless, the stethoscope's commonality should not diminish its importance to the delivery of medical services. For example, during an operation it is critical to the anesthesiologist to closely monitor the patient's breathing and/or heart rate. Most often, auditory monitoring is performed by placing the stethoscope on the chest wall, which is known as precordial monitoring.

The prior art is filled with improvements to the stethoscope to better adapt it for use in a modern health care environment. U.S. Pat. No. 4,777,961 to Saltzman and U.S. Pat. No. 5,027,825 to Phelps, Sr. et al. both illustrate stethoscopes that use electronics to convert sound from the patient into radio signals that are transmitted for reception by a remote receiver. While these two patents illustrate highly sophisticated and expensive stethoscopes, U.S. Pat. No. 4,991,686 to Allen discloses a traditional stethoscope that is made entirely of plastic and can thus be disposed of after use to discourage the spread of disease. Still another improvement to the traditional stethoscope is an improved head that is more efficient at capturing sound from the patient's body. U.S. Pat. No. 5,420,382 to Katz describes a stethoscope where the head is constructed from a sea shell because of the shell's inherent ability to enhance the fidelity of any received sound.

While these inventions have all made valuable improvements to the stethoscope, there is still room for improvement in the art.

SUMMARY OF THE INVENTION

One object of the present invention is to provide a lightweight, economical precordial monitor.

Another object is that the monitor be capable of monitoring a patient's heart or breathing rate.

A further object is that the monitor be capable of simultaneously monitoring a patient's skin temperature while also monitoring a patient's heart or breathing rate.

According to the present invention, the foregoing and other objects and advantages are attained by a precordial monitor including a head that has a chamber for capturing sound from a patient's body. The head has an acoustic probe for detecting the sound captured in the chamber and a temperature sensor for measuring the skin temperature of the patient.

In accordance with one aspect of the invention, the monitor is attached to the patient's body with an adhesive In accordance with another aspect of the invention, transmission means is provided to carry the sound from the acoustic probe to an earpiece.

In accordance with yet another aspect of the invention, the temperature sensor is a thermistor with wires extending therefrom for determining the patient's skin temperature based on variations in the electrical resistance of the thermistor.

It is yet a further object of this invention to provide a precordial monitor which is latex-free.

Additional objects and advantages will become apparent from a consideration of the following description and drawings.

DETAILED DESCRIPTION

With reference to the figures, an apparatus that achieves all the various objects of the present invention will now be described.

Figure 1:
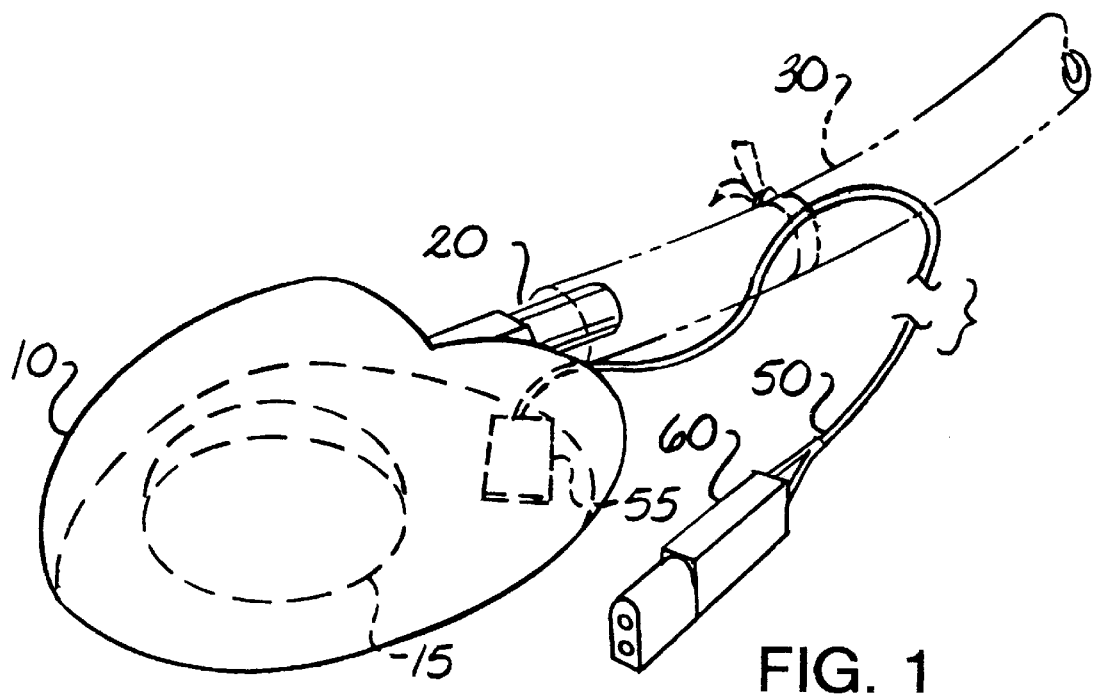
FIG. 1 is a perspective view of a precordial monitor according to the present invention.

FIG. 1 shows a perspective view of a preferred embodiment for a precordial monitor according to the present invention. The monitor includes head 10 that is placed against a patient's body to monitor either the patient's breathing or heart rate. Advantageously, head 10 can be made from closed cell foam, open cell foam, plastic or other lightweight material. Head 10 is commonly produced through injection molding or thermoforming to generate a desired shape. For the best acoustic response, head 10 is made from a closed cell foam as that material minimizes the number of air pockets in the structure which tend to absorb sound. Traditionally, stethoscope heads are made from a heavy gauge steel so that the weight of the head provides a secure seal with the patient's body thereby minimizing any loss of sound. However, the additional weight makes traditional stethoscope heads much less desirable for applications where the head is not supported by the patient's body. For example, an operation involving the front, upper torso may require the stethoscope to be secured to the patient's side because of space and access considerations. A traditional stethoscope head would require significant amounts of adhesive tape to hold the head to the patient's side. By contrast, lightweight head 10 of the instant invention readily secures to any portion of a patient's upper torso.

Figure 2:
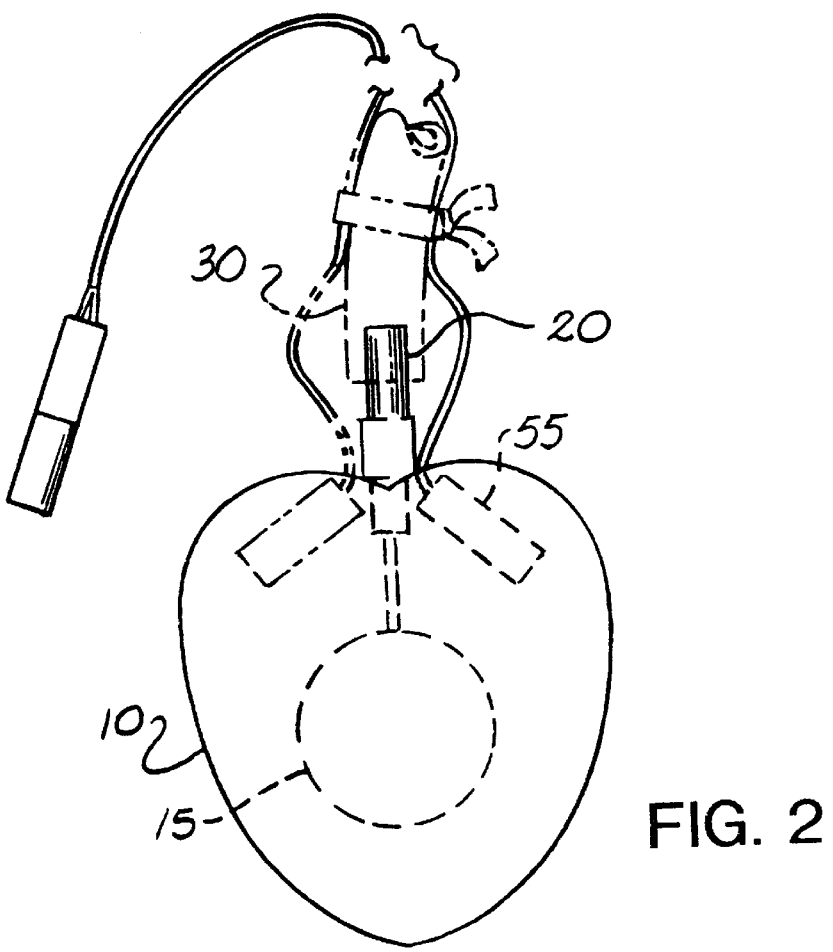
FIG. 2 is an elevation view of a precordial monitor according to the present invention.
Figure 3:
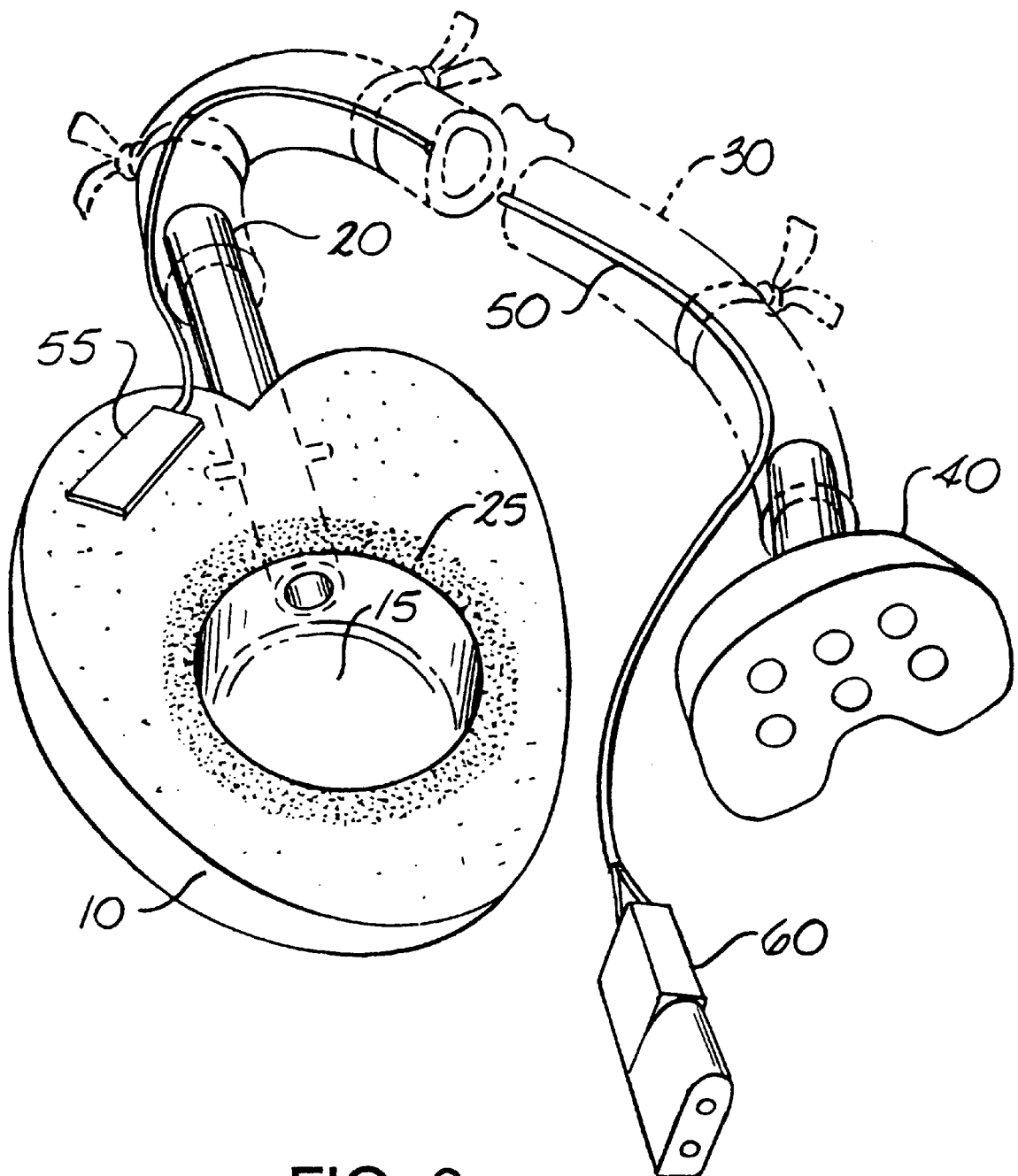
FIG. 3 is a view showing the underside of a precordial monitor according to the present invention.

Head 10 contains chamber 15, as shown in FIGS. 2 and 3, that is used to capture the acoustic waveforms generated by the patient's body. The shape of chamber 15 within head 10 is preferably designed for enhanced acoustical characteristics. In practice, the chamber may be fitted with a material that reflects acoustic waves if head 10 is made from a soft material that tends to absorb sound. Alternatively, embodiments made of a foam-like material should have a substantially non-porous surface associated with chamber 15.

To transmit the sound captured in chamber 15, acoustic probe 20 is lodged in head 10 and extends therefrom as shown in FIGS. 1, 2 and 3. Acoustic probe 20 interfaces with chamber 15 to detect the acoustic waveforms and provides an external interface on which flexible tubing 30 can be attached to carry the sound to earpiece 40 as shown in FIG. 3. In the embodiment shown, acoustic probe 20 is merely a plastic channel for funneling sound up through tubing 30 to earpiece 40. It is envisioned that alternative probes could be used that employ sophisticated electronics to convert the sound to an electrical signal that could then be amplified and either transmitted over a wire or sent via radio signal to an earpiece or receiver.

In addition to monitoring breathing and heart rates, the precordial monitor can also monitor a patient's skin temperature. As shown in FIG. 3, head 10 contains a recessed region where temperature sensor 55 is attached. Temperature sensor 55 is usually a standard thermistor (as illustrated in FIGS. 1 and 3) whose resistance varies with temperature. However, any type of temperature sensor capable of attachment to head 10 could be employed. A pair of wires 50 extend from sensor 55 and terminate in socket 60 for attachment to a translation unit that converts the measured electrical resistance of sensor 55 to a temperature. However, a separate sensor could be used with the precordial monitor Further, additional sensor space can be provided as seen by a second sensor 55.

Finally, head 10 includes an integral ring of adhesive 25 around the opening of chamber 15 for securing the precordial monitor to the patient's body. By positioning adhesive 25 around the opening of chamber 15, a tight seal is made between chamber 15 and the patient's body ensuring a minimal loss of sound.

The resulting precordial monitor is particularly useful with neonatal care. The monitor is extremely light-weight, can be secured and maintained to a patient's side or other non-horizontal surface, and can be supplied in a latex-free configuration. The compact shape minimizes obstructions to the surgical area of a patient. In addition, an integral temperature sensor further simplifies the surgical environment.

The above description is given in reference to a precordial monitor that can be used to monitor a patient's breathing rate, heart rate and skin temperature. However, it is understood that many variations are apparent to one of ordinary skill in the art from a reading of the above specification and such variations are within the spirit and scope of the invention as defined by the following appended claims:

That which is claimed:

1. A precordial monitor comprising:
   a head having an open chamber for capturing acoustic waveforms via placement of said head on a patient's body;
   an acoustic probe held by said head and in acoustic communication with said open chamber for detecting said acoustic waveforms; and
   a temperature sensor secured within a recessed region defined by said head for measuring said patient's temperature via placement of said head on said patient's body.

2. The precordial monitor of claim 1 further comprising means for securing said head to said patient's body.

3. The precordial monitor of claim 2 wherein said means for securing said head to said patient's body is double sided adhesive tape.

4. The precordial monitor of claim 1 further comprising:
   an earpiece; and
   means for transmitting said acoustic waveforms detected by said acoustic probe to said earpiece.

5. The precordial monitor of claim 1 wherein said temperature sensor is a thermistor.

6. The precordial monitor of claim 1 wherein said head is made from closed cell foam.

7. The precordial monitor of claim 1 wherein said head further comprises an adhesive surrounding said opening.

* * * * *